(12) United States Patent
McRee et al.

(10) Patent No.: US 7,158,888 B2
(45) Date of Patent: Jan. 2, 2007

(54) DETERMINING STRUCTURES BY PERFORMING COMPARISONS BETWEEN MOLECULAR REPLACEMENT RESULTS FOR MULTIPLE DIFFERENT BIOMOLECULES

(75) Inventors: Duncan McRee, San Diego, CA (US); Peter R. David, Palo Alto, CA (US); Frank von Delft, San Diego, CA (US); John Rammelkamp, La Jolla, CA (US); Enrique Abola, Encinitas, CA (US)

(73) Assignee: Takeda San Diego, Inc., San Diego, CA (US)

(*) Notice: Subject to any disclaimer, the term of this patent is extended or adjusted under 35 U.S.C. 154(b) by 290 days.

(21) Appl. No.: 09/848,866

(22) Filed: May 4, 2001

(65) Prior Publication Data

US 2002/0183861 A1    Dec. 5, 2002

(51) Int. Cl.
G06F 17/11    (2006.01)
G06F 17/50    (2006.01)
G06F 19/00    (2006.01)

(52) U.S. Cl. .................. 702/19; 702/27; 703/12
(58) Field of Classification Search ............. 702/19, 702/27; 703/12
See application file for complete search history.

(56) References Cited

U.S. PATENT DOCUMENTS

| | | |
|---|---|---|
| 5,118,937 A | 6/1992 | Hillenkamp et al. .......... 250/282 |
| 5,375,207 A | 12/1994 | Blakely et al. |
| 5,436,850 A | 7/1995 | Eisenberg et al. |
| 5,544,254 A | 8/1996 | Hartley |
| 5,544,256 A | 8/1996 | Brecher |
| 5,600,833 A | 2/1997 | Senn et al. |
| 5,164,831 A | 3/1997 | Edvardsson |
| 5,859,623 A | 1/1999 | Meyn |
| 5,859,927 A | 1/1999 | Adams |
| 5,859,972 A | 1/1999 | Subramaniam et al. |
| 5,878,373 A | 3/1999 | Cohen et al. |
| 6,057,159 A | 5/2000 | Lepre |
| 6,060,293 A | 5/2000 | Bohr et al. ............... 435/173.1 |
| 6,064,754 A | 5/2000 | Parekh et al. ............... 382/129 |
| 6,148,878 A | 11/2000 | Ganz |

(Continued)

FOREIGN PATENT DOCUMENTS

WO    WO 9904361 A1    1/1999

(Continued)

OTHER PUBLICATIONS

Vagin et al. Acta Crystallographica, Section D: Biological Crystallography (2000), D56(12), 1622-1624.*

(Continued)

*Primary Examiner*—Michael Borin
(74) *Attorney, Agent, or Firm*—David J. Weitz

(57) ABSTRACT

A method is provided for identifying a search model to use in molecular replacement for determining a structure of a target biomolecule, such as a protein, from X-ray diffraction data, the method comprising: employing computer executable logic to perform multiple molecular replacement searches on X-ray diffraction data of the target biomolecule where a group of different biomolecule structures are used as search models for the multiple molecular replacement searches; and employing computer executable logic to compare solutions from the multiple molecular replacement searches, the comparison producing data from which biomolecule structures can be identified as having superior structural identity with the target biomolecule as compared to the other biomolecule structures in the group.

57 Claims, 3 Drawing Sheets

U.S. PATENT DOCUMENTS

| | | |
|---|---|---|
| 6,240,374 B1 | 5/2001 | Cramer et al. |
| 6,360,792 B1 | 3/2002 | Ganz |
| 6,368,402 B1 | 4/2002 | DeTitta |
| 6,402,837 B1 | 6/2002 | Shtrahman |
| 6,529,612 B1 | 3/2003 | Gester |
| 6,558,623 B1 | 5/2003 | Ganz |
| 2001/0001732 A1 | 5/2001 | Mitsuiki |
| 2002/0001404 A1 | 1/2002 | Yoshikawa et al. |
| 2002/0029814 A1 | 3/2002 | Unger et al. |
| 2002/0144738 A1 | 10/2002 | Unger et al. |
| 2002/0169512 A1 | 11/2002 | Steward |
| 2002/0182637 A1 | 12/2002 | Santarsiero et al. |
| 2003/0000597 A1 | 1/2003 | Ganz et al. |
| 2003/0075101 A1 | 4/2003 | Weigl et al. |
| 2003/0099382 A1 | 5/2003 | Ganz et al. |
| 2004/0135788 A1 | 7/2003 | Davidson et al. |
| 2003/0150375 A1 | 8/2003 | Segelke et al. |
| 2004/0215398 A1 | 10/2004 | Mixon |
| 2004/0218804 A1 | 11/2004 | Affleck et al. |

FOREIGN PATENT DOCUMENTS

| | | |
|---|---|---|
| WO | WO 01/09595 A2 | 2/2001 |
| WO | WO 01/09595 A3 | 2/2001 |
| WO | WO 01/54061 A2 | 7/2001 |
| WO | WO 01/54061 A3 | 7/2001 |
| WO | WO 02/09139 A2 | 11/2002 |
| WO | WO 03/032558 A2 | 4/2003 |
| WO | WO 03/032558 A3 | 4/2003 |
| WO | WO 03/034030 A2 | 4/2003 |
| WO | WO 03/034030 A3 | 4/2003 |
| WO | WO 03/064047 A1 | 8/2003 |

OTHER PUBLICATIONS

Podjarny, A. et al.Transactions of the American Crystallographic Association, 1996, vol. Date 1994, 30, 109-120.*

Vitali et al. Database Caplus, DN 108:36081. Journal of Molecular Biology, 1987, 198(2), 351-5.*

Chen et al. Structure,2000, vol. 8, R213-R220.*

Kissinger et al. Acta Crystallographica Section D, Biological Crystallography, 1999, D55, 484-491.*

Berman, Helen et al., The Protein Data Bank, Nucleic Acids Research, 2000, vol. 28, No. 1, 235-242.

Foadi, J. et al., A flexible and efficient procedure for the solution and phase refinement of protein structures, Acta Cryst. (2000), D56, 1137-1147.

Gray, Peter M.D. et al., Macromolecular structure information and databases, TIBS 21 (Jul. 1996), pp. 251-254.

Holm, Liisa et al., Protein Structure Comparison by Alignment of Distance Matrices, J. Mol. Biol. (1993) 233, 123-138.

Mochalkin, Igor et al., "High-Throughput Structure Determination in an Informatics Environment", http://www.acceltys.com/webzine (Aug. 1, 2002), 4 pages.

Murzin, Alexey G. et al., SCOP: A Structural Classification of Proteins Database for the Investigation of Sequences and Structures, J. Mol. Biol. (1995) 247, 536-540.

Navaza, J., *AmoRe*: an Automated Package for Molecular Replacement, Acta. Cryst. (1994), A50, 157-163.

Robinson, Daniel D., Partial Molecular Alignment via Local Structure Analysis, J. Chem. Int. Comput. Sci. 2000, 40, 503-512.

U.S. Appl. No. 10/413,418, filed Apr. 11, 2003, Boorman et al.

U.S. Appl. No. 10/413,420, filed Apr. 11, 2003, Boorman et al.

U.S. Appl. No. 10/413,425, filed Apr. 11, 2002, Boorman et al.

U.S. Appl. No. 10/413,500, filed Apr. 11, 2002, Boorman et al.

U.S. Appl. No. 10/413,502, filed Apr. 11, 2003, Karlak et al.

Broderson, D.E, et al., "Xact,: a program for construction, automated setup and bookkeeping of crystallization experiments", Computer Programs, J. Appl. Cryst. (1999), vol. 32, pp. 1012-1016.

Crystal Monitor Help Document (HTML file created Aug. 6, 2001).

Gilliland, Gary L. et al., Biological Macromolecule Crystallization Database, Version 3.0: New Features, Data and the NASA Archive for Protein Crystal Growth Data, Acta Cryst. (1994), D50, 408-413.

Hodgson, Keith, Biological and Environmental Research Advisory Committee (BERAC) Meeting, Minutes, (May 1-2, 2001), pp. 6-7, http://www.er.doe.gov/production/ober/beract/5-01mins.html, printed on Apr. 12, 2002.

Jurisica, I. et al., "Intelligent decision support for protein crystal growth", IBM Systems Journal (2001), vol. 40, No. 2, pp. 394-409.

Stephens et al. "Sams Teach Yourself on SQL in 21 Days", 4th Edition, 2003, section: Day 1. Getting Started with SQL.

* cited by examiner

DETERMINING STRUCTURES BY PERFORMING COMPARISONS BETWEEN MOLECULAR REPLACEMENT RESULTS FOR MULTIPLE DIFFERENT BIOMOLECULES

FIELD OF THE INVENTION

The present invention relates to methods for determining 3-dimensional structures of biomolecules and more specifically methods for determining structures of biomolecules by molecular replacement using X-ray diffraction data with multiple different search models where the solutions from the multiple different search models are compared.

DESCRIPTION OF RELATED ART

Among the various methods of drug discovery and development, structure-based drug development has become one of the most important approaches, thanks to rapidly advancing computation techniques. It is well recognized that understanding the detailed three-dimensional structure of a protein not only assists in rational drug design and development in the laboratory but also provides a well-defined target in high throughput drug screening by using computer-aided docking analysis. Solving high-resolution structures of proteins in a high throughput fashion presents a major bottleneck in the chain of going from DNA to drug development.

One component of the bottleneck associated with solving high resolution structures involves the generation of protein crystals in a high throughput manner upon which structure determination can be performed. Various methods have been developed for growing crystals suitable for performing structure determination. Examples of these methods include the free interface diffusion method (Salemme, F. R. (1972) Arch. Biochem. Biophys. 151:533–539), vapor diffusion in the hanging or sitting drop method (McPherson, A. (1982) Preparation and Analysis of Protein Crystals, John Wiley and Son, New York, pp 82–127), and liquid dialysis (Bailey, K. (1940) Nature 145:934–935). A few automated crystallization systems have been developed based on the hanging drop methods, for example Cox, M. J. and Weber, P. C. (1987) J. Appl. Cryst. 20:366; and Ward, K. B. et al. (1988) J. Crystal Growth 90:325–339. More recently, a large scale, high-throughput system for performing crystallizations was described in International Patent Publication WO 00/78445, published Dec. 28, 2000, which is incorporated herein by reference in its entirety.

Once proteins are crystallized, the crystals are used to determine high-resolution structures of the proteins. High-resolution structures are most typically solved by X-ray crystallography, and also by using multi-dimensional NMR spectroscopy on high-field NMR machines.

A further component of the bottleneck associated with determining high-resolution structures for proteins is converting X-ray crystal data into solved structures. The so-called "phase problem" results from the inability of X-ray detectors to measure the relative phases of the diffracted X-rays due to fundamental limitations of physics. Thus, various methods have been developed for solving the phase problem including Multiple Isomorphous Replacement (MIR) and Multiple Anomalous Dispersion (MAD). One method for solving a protein or nucleic acid structure from X-ray diffraction data is to identify an atomic model, referred to herein as a "search model", that has structural identity with the protein whose structure is being solved. Once an appropriate search model is selected, it is then necessary to work out how the search model should be oriented and positioned. Molecular replacement encompasses techniques that are used in macromolecular crystallography to determine the orientation and position of a molecule using a previously solved structure as the search model. Molecular replacement, when possible, has significant economies over MIR and MAD. For example, it requires lower resolution data (15–4 Ångstrom data) to find a solution. MIR typically requires searching a large number of soaking conditions to identify derivatives which can use a large amount of material and time. MAD requires a synchrotron and the introduction of an anomalous scatterer (typically selenium methionine) which can be expensive and difficult.

Molecular replacement is generally a six dimensional problem consisting of three rotational and three translational parameters. This can be approximated by separating molecular replacement into two successive stages, namely a rotation search followed by a translation search at a fixed rotation. If successful, a preliminary model of the structure of the protein whose structure is being solved (the target) is obtained by correctly orienting and positioning a search model (a related protein structure of different sequence but similar structure). This solution can be further optimized by rigid body refinement. Finally, the resultant structure can be put through cycles of map calculation, model fitting and refinement to remove the bias introduced by the starting search model and produce the final, solved structure. Even in the absence of a suitable search model, the self-rotation function in molecular replacement can be used to determine the direction and nature of non-crystallographic symmetry elements.

Positioning the atomic model in its optimal orientation ($\underline{x}'$) involves determining a rotation matrix, [C], and a translation vector, $\underline{d}$, to apply to the starting co-ordinates of the search model, $\underline{x}$. Hence, $\underline{x}'=[C]\underline{x}+\underline{d}$.

Several software programs have been developed for identifying crystallographic molecular replacement solutions. These programs perform molecular replacement calculations to perform an efficient six-dimensional search. In the original method developed by Rossman (The Molecular Replacement Method (1972), International Science Series vol. 13), the search is broken into two steps, a rotational search followed by a translational search. Thus, the problem was reduced to two successive 3-dimensional searches that requires far less time than a full 6-dimensional search. An excellent review of the methods as practiced today can be found in E. Lattman, Methods. Enzmology v. 115, pp. 55–57 (1985). Even with today's faster computers, the full 6-dimensional search is still very slow, although it can be used.

Another algorithm, implemented in the program, EPMR, finds crystallographic molecular replacement solutions using an evolutionary search algorithm. The program directly optimizes the three rotational and three positional parameters for the search model with respect to the correlation coefficient between Fo and Fc and is very rapid compared to a full 6-dimensional search. A second advantage is that it is an easily automated algorithm as it does not require operator intervention to determine if a solution has been found as in the older methods.

EPMR works by gradually optimizing a population of initially random molecular replacement solutions with respect to the correlation coefficient between observed and calculated structure factors. This approach has been found to be several orders of magnitude faster than more systematic six-dimensional searches. Comparisons with conventional molecular replacement techniques indicate that solutions can be found by EPMR using significantly less accurate or less complete search models.

EPMR is described in "Rapid, Automated Molecular Replacement Using an Evolutionary Search Algorithm." Acta Crystallographica D55, pp. 484–491 (1999), Charles R. Kissinger, Daniel K. Gehlhaar and David B. Fogel*, Agouron Pharmaceuticals, Inc. 3565 General Atomics Court, San Diego, Calif. 92121 and * Natural Selection, Inc., 1591 Calle de Cinco, La Jolla, Calif. 92037. Although the present invention will be described herein in greater detail with regard and reference to use of the EPMR program, it is noted that the present invention is compatible with results from any molecular replacement program, whether in existence or developed in the future.

A correlation coefficient is typically used to judge the correctness by comparing the amplitudes calculated from a given orientation, Fc, with the observed amplitudes, $$C = \frac{\sum (Fo - \overline{Fo})(Fc - \overline{Fc})}{\sqrt{\sum (Fo - \overline{Fo})^2 \sum (Fc - \overline{Fc})^2}}$$

or a second correlation formula C2 is sometimes also used, $$C2 = \frac{\sum FoFc}{\sqrt{\sum Fo^2 \sum Fc^2}}$$

A chief difficulty in molecular replacement is determining the accuracy of a given orientation solution. First, the search model may not be close enough to the unknown structure and even if the best orientation is found, it may not produce usable phases. Secondly, the top solution may be erroneous, even if a full search is done. Part of the difficulty lies in the lack of a statistically reliable method of measuring the probability of the correctness of a given solution. A large part of the difficulty lies in the fact that the absolute value of the correlation coefficient is dependent on a number of factors besides the correctness of the solution and thus there is a large "gray area" of correlation coefficient values where the solution may or may not be correct. In order to address these problems, the present invention provides a method for assessing the validity of a solution from its correlation coefficient. It should be noted that even if the molecular replacement program used does not provide a correlation coefficient in its output, the correlation coefficient, or any other figure of merit, can be computed in a separate step, post facto.

SUMMARY OF THE INVENTION

A method is provided for identifying a search model to use in molecular replacement for determining a structure of a target biomolecule, such as a protein from crystal data. In one embodiment, the method comprises employing computer executable logic to perform multiple molecular replacement searches on crystal data of the target biomolecule where a diverse group of different biomolecule structures are used as search models for the multiple molecular replacement searches; and employing computer executable logic to compare solutions from the multiple molecular replacement searches, the comparison producing data from which biomolecule structures from the group can be identified as having superior structural identity with the target biomolecule as compared to the other biomolecule structures in the group.

A method is also provided for identifying a search model to use in molecular replacement for determining a structure of a target biomolecule, such as a protein, from X-ray diffraction data. In one embodiment, the method comprises employing computer executable logic to perform multiple molecular replacement searches on crystal data of the target biomolecule where a group of different biomolecule structures are used as search models for the multiple molecular replacement searches; and employing computer executable logic to identify a biomolecule structure from the group whose use as a search model produces a molecular replacement solution that is superior to the molecular replacement solutions produced by the other biomolecule structures in the group.

A method is also provided for determining a structure of a target biomolecule, such as a protein, from X-ray diffraction data. In one embodiment, the method comprises employing computer executable logic to perform multiple molecular replacement searches on crystal data of the target biomolecule where a group of different biomolecule structures are used as search models for the multiple molecular replacement searches; employing computer executable logic to identify a biomolecule structure from the group whose use as a search model produces a molecular replacement solution that is superior to the molecular replacement solutions produced by the other biomolecule structures in the group; and employing computer executable logic to determine a structure for the target biomolecule employing the identified biomolecule structure.

A method is also provided for identifying a search model to use in molecular replacement for the determination of a structure of a target biomolecule, such as a protein, from crystal data. In one embodiment, the method comprises: (a) employing computer executable logic to perform multiple molecular replacement searches on crystal data of the target biomolecule using multiple different structures as search models; (b) employing computer executable logic to compare the resulting molecular replacement solutions in order to identify a biomolecule structure whose use as a search model produces a molecular replacement solution that is superior to the molecular replacement solutions of other biomolecule structures upon which the molecular replacement searches were performed; and (c) if none of the molecular replacement solutions are comparatively better, evaluating additional biomolecule structures by repeating steps (a) and (b) with the additional biomolecule structures until a biomolecule structure is identified which produces a molecular replacement solution that is superior to the molecular replacement solutions of other biomolecule structures upon which the molecular replacement searches were performed.

According to each of the above methods, although these methods are described herein primarily with regard to X-ray diffraction data, it should be noted that other forms of data can also be employed other than X-ray diffraction data. For example, neutron diffraction data, nuclear magnetic resonance data, and mass spectroscopy data may also be employed.

According to each of the above methods, although these methods are specified to some degree with regard to the use of molecular replacement to determine the structure of a target protein from diffraction data, it is noted that each of these methods may be more broadly applied to solving the 3-dimensional structures of biomolecules such as protein, DNA, RNA and complexes comprising one or more biomolecules. As used herein, the term biomolecule is intended to encompass proteins, DNA, RNA, and complexes comprising proteins, DNA and/or RNA.

According to any of the methods, comparing molecular replacement solutions may comprise comparing figures of merit calculated for the molecular replacement solutions.

According to any of the methods, comparing molecular replacement solutions may comprise performing a statistical analysis on figures of merit calculated for the molecular replacement solutions.

According to any of the methods, comparing molecular replacement solutions may comprise determining which of the biomolecule structures produced a molecular replacement solution whose figure of merit is at least two, three, four, five, ten or more standard deviations better than the average figure of merit for molecular replacement solutions for the biomolecule structures in the group.

According to any of the methods, comparing molecular replacement solutions may comprise comparing root mean square errors for each molecular replacement solution of a probability-weighted average over all possible phase choices.

According to any of the methods, comparing molecular replacement solutions may comprise establishing a background correlation level between the biomolecule structures and the target biomolecule based on the molecular replacement solutions and determining which of the biomolecule structures produced a molecular replacement solution that exceeds the background correlation level by two, three, four, five, ten or more standard deviations.

According to any of the methods, the group of different biomolecule structures on which molecular replacement searches are performed may comprise at least 3, 4, 5, 10, 15, 25, 50, 100, 200, 500, or more different biomolecule structures.

According to any of the methods, the group of different biomolecule structures on which molecular replacement searches are performed may comprise at least 0.1%, 1%, 5%, 10%, 20%, 30%, 40%, 50%, 75% or more of the protein structures stored in the Protein Data Bank.

According to any of the methods, the group of different biomolecule structures on which molecular replacement searches are performed may comprise at least 2, 3, 4, 5, 10, 15, 25, 50, 100, 200, 500, or more different biomolecule structures that are structurally unrelated to the target protein.

According to any of the methods, the group of different biomolecule structures on which molecular replacement searches are performed may comprise at least 1, 2, 3, 4, 5, 10, 15, 25, 50, 100 different protein structures that have less than 70%, preferably less than 50%, more preferably less than 40%, and most preferably less than 25% sequence identity with the target protein.

According to any of the methods, the group of different biomolecule structures on which molecular replacement searches are performed may comprise at least 2, 3, 4, 5, 10, 15, 25, 50, 100, 200, 500, or more different biomolecule structures that are structurally unrelated to each other.

According to any of the methods, the group of different biomolecule structures on which molecular replacement searches are performed may comprise at least 2, 3, 4, 5, 10, 15, 25, 50, 100, 200, 500, or more different proteins that each have less than 70%, preferably less than 50%, more preferably less than 40%, and most preferably less than 25% sequence identity with at least one other protein in the group.

According to any of the methods, the group of different biomolecule structures on which molecular replacement searches are performed may comprise at least 1, 2, 3, 4, 5, 10, 15, 25, 50, 100, 200, 500, or more different biomolecule structures that are predicted structures for a biomolecule.

According to any of the methods, the group of different biomolecule structures on which molecular replacement searches are performed may comprise at least 1, 2, 3, 4, 5, 10, 15, 25, 50, 100, 200, 500, or more different biomolecule structures where at least a portion of the native structure of the biomolecule has been removed.

According to any of the methods, the group of different biomolecule structures on which molecular replacement searches are performed may comprise at least 1, 2, 3, 4, 5, 10, 15, 25, 50, 100, 200, 500, or more different biomolecule structures which comprise a combination of two or more structure fragments.

According to any of the methods, the data produced from the comparison may identify which biomolecule structures produced molecular replacement solutions that are at least among the top 35%, 30%, 20% 10%, 5%, 2%, 1% of molecular replacement solutions produced by the group.

According to any of the methods, the data produced from the comparison may identify which biomolecule structures produced molecular replacement solutions that are at least two, three, four, five, ten or more standard deviations better than the average molecular replacement solution produced by the group.

According to any of the methods, the method may further comprise employing computer executable logic to select the group of different biomolecule structures used to perform the multiple molecular replacement searches.

Selection of the group of biomolecule structures may be based, at least in part, on sequence identity between the biomolecule structure and the target biomolecule.

Selection of the group of biomolecule structures may be at least partially random or completely random.

Selection of the group of biomolecule structures may also be iterative. For example, selection of members of a group of biomolecule structures may be performed until a biomolecule structure is selected whose molecular replacement solution is at least two, three, four, five, ten or more standard deviations better than the average molecular replacement solution for the biomolecule structures in the group.

Selection of the group of biomolecule structures may comprise selecting at least 0.1%, 1%, 5%, 10%, 20%, 30%, 40%, 50%, 75% of the structures stored in the Protein Data Bank.

Selection of the group of protein structures may comprise selecting at least 1, 2, 3, 4, 5, 10, 15, 25, 50, 100 different biomolecule structures that have less than 70%, preferably less than 50%, more preferably less than 40%, and most preferably less than 25% sequence identity with the target biomolecule.

Selection of the group of biomolecule structures may comprise selecting at least 2, 3, 4, 5, 10, 15, 25, 50, 100, 200, 500, or more different biomolecule structures that are structurally unrelated to each other.

Selection of the group of biomolecule structures may comprise selecting at least 2, 3, 4, 5, 10, 15, 25, 50, 100, 200, 500, or more different biomolecules that each have less than 70%, preferably less than 50%, more preferably less than 40%, and most preferably less than 25% sequence identity with at least one other biomolecule in the group.

Selection of the group of biomolecule structures may comprise selecting one or more predicted structures of biomolecules.

Selection of the group of biomolecule structures may also comprise selecting one or more partial structures of biomolecules.

Selection of the group of biomolecule structures may also comprise selecting combinations of two or more structure fragments of biomolecules.

Molecular replacement may be performed by any program capable of performing molecular replacement. Examples of such programs include, but are not limited to EPMR, AMORE, MERLOT, GLRF, BRUTE, XTALVIEW, ENVELOPE, FFSYNTH, FFTINV, and RECIP. In one variation, the molecular replacement program comprises an evolutionary algorithm for searching six-dimensional space.

It is noted that computer readable medium is also provided that is useful in association with a computer which includes a processor and a memory, the computer readable medium encoding logic for performing any of the computer executable methods described herein. Computer systems for performing any of the methods are also provided, such systems including a processor, memory, and computer executable logic that is capable of performing one or more of the computer executable methods described herein

DETAILED DESCRIPTION OF THE INVENTION

Figure 1:
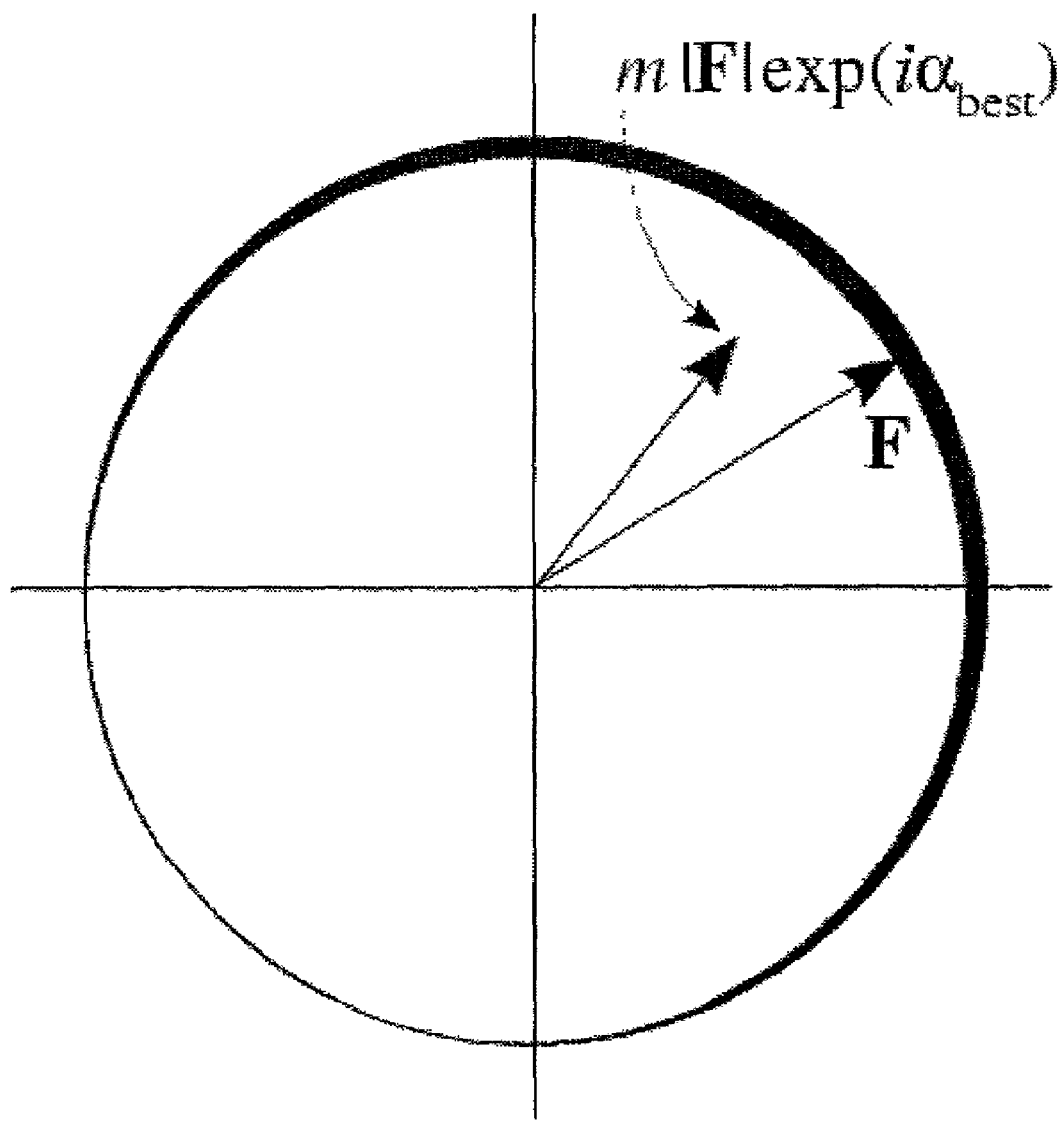
FIG. 1 illustrates the process of taking a probability-weighted average.

The present invention relates to methods and computer executable logic for determining high-resolution structures for biomolecules such as proteins, DNA, RNA, as well as biomolecule complexes comprising protein, DNA and/or RNA by converting crystal data into solved structures.

According to the present invention, methods and computer executable logic are provided for performing multiple molecular replacement searches where a different biomolecule or biomolecule complex structure, for example a protein, is used as a search model for each molecular replacement search. The molecular replacement solutions derived using the multiple different biomolecule or biomolecule complex structures as search models are then compared with each other in order to select which biomolecule or biomolecule complex structure has superior structural identity with the biomolecule whose structure is being solved. In one embodiment, comparing figures of merit for the different molecular replacement solutions forms the comparison. It is noted, however, that any comparison method may be employed which compares the relative structural identities of different search models to a biomolecule or biomolecule complex whose structure is being solved based on molecular replacement solutions.

A biomolecule or biomolecule complex structure identified as having superior structural identity may then be used as the search model for solving the biomolecule or biomolecule complex structure.

For convenience, the present invention is described herein to some degree in relation to solving protein structures. However, it is emphasized that the invention can be more broadly applied to any type of biomolecule such as proteins, DNA, RNA or biomolecule complexes comprising protein, DNA and/or RNA for which structures are available for molecular replacement and comparison. For example, the invention is useful for individual protein structures as well as binding studies or studies of complexes formed from previously-determined proteins.

Comparing the solutions from molecular replacement searches using multiple different biomolecule structures as search models provides several significant advantages.

Without comparing molecular replacement solutions, one cannot be sure that a given search model has significant structural identity with the biomolecule or biomolecule complex whose structure is being solved. Rather, search models have been mistakenly relied upon as being good models for a given biomolecule or biomolecule complex when they are in fact poor search models for that biomolecule or biomolecule complex. Even after a search model is selected and molecular replacement is performed, it is difficult absent performing comparisons according to the present invention to be confident that the selected search model has sufficient structural similarity to yield an accurate structure. As a result, a level of doubt inherently surrounds any structural solution where a comparison between solutions is not performed.

By contrast, comparing molecular replacement solutions allows one to determine that a given search model is superior to the other search models tested. More specifically, given that very few search models will have significant structural identity with the biomolecule or biomolecule complex whose structure is being solved, comparison of molecular replacement solutions according to the present invention allows one to establish a background correlation level based on a statistically significant number of structures that do not match. This makes it possible to readily identify superior search models by looking for a significantly greater correlation than the background correlation level. By being able to evaluate how much superior a given search model is relative to other search models, one is also able to infer whether any of the search models have significant structural identity with the biomolecule or biomolecule complex whose structure is being solved. This thus allows one to select which search model to use as the search model for molecular replacement.

As is discussed further herein, figures of merit are commonly used as a way to quantify how good a molecular replacement solution is. However, figures of merit vary greatly from structure comparison to structure comparison. It is thus often difficult to determine if any given molecular replacement solution is a good or reasonable solution. By performing multiple molecular replacement searches according to the present invention, in particular using search structures thought to be unrelated to the target, the figures of merit can be compared. For example it is possible to directly or indirectly normalize the figures of merit produced. By knowing the distribution of the figures of merit produced from performing molecular replacement on multiple structures, one is able to identify molecular replacement solutions that are statistically superior even though their individual values might appear poor or fair upon individual inspection. Absent the comparison provided by the present invention, these solutions would commonly be overlooked.

Comparing molecular replacement solutions also allows one to determine that none of the search models are superior to the other search models tested. For example, one is able to identify molecular replacement solutions that are not statistically superior even though their individual figures of merit might appear good or excellent upon individual inspection. Absent the present invention, these solutions would commonly be used even though the search models are not actually worth utilizing as a potential solution.

By recognizing through a comparison of molecular replacement solutions that none of the search models tested have the requisite structural identity with the biomolecule or biomolecule complex whose structure is being solved, one is able realize that additional work needs to be done in order to identify a suitable search model for solving the biomolecule or biomolecule complex structure. This may involve testing additional structures. It may also involve testing substructures or structure fragments in an effort to find a search model that has the requisite structural identity.

A further advantage provided by comparing molecular replacement results according to the present invention is that it not only allows one to select the best search models, it also allows one to select the resolutions at which molecular replacement solution comparisons should be made. Figures of merit used to compare molecular replacement search results are dependent upon both the resolution of the X-ray crystallographic data used and the resolutions over which comparisons are made. Hence, it is desirable to select resolutions that can be effectively used to make accurate comparisons. By comparing figures of merit for multiple different molecular replacement searches at multiple different resolutions, the present invention not only allows one to select the best search model to use, the present invention also allows one to select which resolutions are most useful for making comparisons between figure of merit, and which resolutions are not.

Yet a further advantage provided by comparing molecular replacement results according to the present invention is that the selection of superior search models reduces the need to perform additional steps of structure refinement and optimization. Molecular replacement is used to produce an aligned model for an unknown structure. Prior to the present invention, additional steps of structure refinement and optimization were typically performed to improve the aligned model. This is because the starting atomic model used to perform molecular replacement is typically less than optimal. For example, additional experimental data sets are frequently needed whose generation is time consuming, expensive and labor intensive. Heavy atom derivatives of the unknown structure and minor modifications for anomalous phasing, such as selenomethionine modified proteins, frequently need to be produced. By being able to select superior search models according to the present invention, the need for such additional steps of structure refinement and optimization can be reduced and/or eliminated.

According to the present invention, an iterative search is optionally performed to identify a suitable search model. For example, one may (a) perform molecular replacements using multiple different structures as search models, (b) compare the resulting molecular replacement solutions in order to evaluate whether any of the structures have superior structural identity with the biomolecule or biomolecule complex whose structure is being solved, and, if none of the search models have superior structural identity, (c) evaluate additional structures by repeating (a) and (b) with the additional structures until a comparison between molecular replacement solutions reveals that a particular search model has superior structural identity with the biomolecule or biomolecule complex whose structure is being solved. In one variation, superior structural identity refers to a biomolecule or biomolecule complex structure whose molecular replacement solution is at least two, three, four, five, ten or more standard deviations better than the other biomolecule or biomolecule complexes tested.

The ability to use a comparison between molecular replacement solutions to determine whether any of the different biomolecule or biomolecule complex structures tested have superior structural identity and thus may be used as a search model allows one to rapidly screen a large number of different biomolecule or biomolecule complex structures for the purpose of identifying a biomolecule or biomolecule complex structure to use as a search model in molecular replacement. This avoids the need that otherwise exists in the art to carefully select an appropriate search model prior to performing molecular replacement.

Previously, in order to solve a biomolecule or biomolecule complex structure, one would first identify a search model for the biomolecule or biomolecule complex that has structural identity with the biomolecule or biomolecule complex. Once an appropriate search model is selected, molecular replacement would be performed to determine how the model should be oriented and positioned.

Search models are typically obtained by selecting a biomolecule or biomolecule complex whose known structure correlates with the structure of the biomolecule or biomolecule complex whose structure is being solved. The need to select a known biomolecule or biomolecule complex structure that correlates with the structure of a biomolecule or biomolecule complex whose structure has not yet been solved creates a significant logistical problem.

To overcome this logistical problem, one would typically use the known structure of a related biomolecule or biomolecule complex or the known structure of the same biomolecule or biomolecule complex from a different crystal form. However, crystal structures of the same or related biomolecule or biomolecule complexes are not always available. Even if the crystal structures of the same or related biomolecule or biomolecule complexes are available, these models do not always correlate well with the structure of the biomolecule or biomolecule complex being solved.

In the case of proteins, historically sequence similarity and predicted secondary structures, such as -helix and -sheet, have been used as an imperfect indicator of structural similarity. If one used sequence identity as the proxy for structural identity, a protein with reasonable sequence identity (i.e. >25%) was typically selected in order to insure there was a decent chance of success. This is because the level of resemblance of two protein structures typically correlates with the level of sequence identity. As a result, scientists have relied on sequence identity to evaluate whether or not molecular replacement will succeed before even trying it. It is noted, however, that proteins with virtually random sequence identities have been found to be suitable search models. This evidences the difficult predictability of using sequence identity as a proxy for structural identity.

Unlike the prior art that presupposes that one is able to select a suitable search model, the present invention uses molecular replacement as a mechanism for identifying the search model to use. This obviates the need to carefully select the search model prior to performing molecular replacement. Rather the solutions from molecular replacement provide a basis for comparing different potential search models.

Because the present invention allows one to simply perform molecular replacement searches on all or a portion of a biomolecule or biomolecule complex structure database, such as the Protein Data Bank, and then determine by comparing the results which search model has a molecular replacement solution with superior structural correlation to the biomolecule or biomolecule complex whose structure is being solved, the present invention allows one to automate the selection of search models to perform molecular replacement upon and the identification of superior search models from those tested.

Molecular replacement searches are preferably performed on at least 3, 4, 5, 10, 15, 25, 50, 100, 200, 500, or more different structures for biomolecule or biomolecule complexes. Selection of the biomolecule or biomolecule complex structures on which molecular replacement is performed may be performed manually or may be automated, i.e., a computer executable logic may be used to select the biomolecule or biomolecule complex structures to test.

Selection of biomolecule or biomolecule complex structures to use as search models may be based on the biomolecule or biomolecule complex being likely to have structural similarity, for example, based on their sequence identities to the protein whose structure is being solved. However, one or more biomolecule or biomolecule complexes are preferably selected that are unlikely to have structural similarity with the biomolecule whose structure is being solved. An unexpected feature of the present invention is that it is actually desirable to perform molecular replacement searches using search models that one would expect to fail, e.g., proteins that would be expected to be structurally dissimilar.

By using search models that are structurally dissimilar, one is able to create a negative basis for comparison. More specifically, as can be seen from FIGS. 2 and 3, the structurally similarity of a structure to a protein whose structure is being solved is made more apparent when the molecular replacement solution derived using that structure is compared to the molecular replacement solutions produced when structures are used that are structurally dissimilar to the protein whose structure is being solved.

An absence of structural similarity to the biomolecule whose structure is being solved may be based on a lack of sequence identity to the biomolecule. Preferably, at least 1, 2, 3, 4, 5, 10, 15, 25, 50, 100, or more structures are selected for performing molecular replacement that are unlikely to have structural similarity with the biomolecule or biomolecule complex whose structure is being solved. In this regard, at least one structure is preferably selected for performing molecular replacement which has less than 70%, preferably less than 50%, more preferably less than 40%, and most preferably less than 25% sequence identity with the biomolecule or biomolecule complex whose structure is being solved.

At least two structures that are unlikely to have structural similarity with each other are also preferably selected for performing molecular replacement. This is because two structures that are unlikely to have structural similarity with each other are unlikely to both have structural similarity with the biomolecule or biomolecule complex whose structure is being solved.

Since the structures of the biomolecules used as search models are known, insuring that two structures are unlikely to have structural similarity with each other can be achieved by comparing their structures. Computer programs such as CL, DALI, STRUCTAL, SSAP, or VAST may be used to perform these comparisons. Alternatively, selection of two structures that are unlikely to have structural similarity with each other may be achieved by selecting at least two structures that have less than 70%, preferably less than 50%, more preferably less than 40%, and most preferably less than 25% sequence identity with each other.

Selection of search models may be partially or completely random. In this regard, computer executable logic may randomly select one or more biomolecule or biomolecule complex structures from a database to use as search models for molecular replacement. Selection of search models may also be sequential, for example based on size, source of origin, or even alphabetically.

A pre-selected group of structures may also be used whose common property is that the structures are unrelated to the other members of the group.

Selection of search models may be iterative where computer executable logic selects one or more biomolecule or biomolecule complex structures, performs molecular replacement, evaluates whether a superior search model has been identified, and if not, repeats the process of selecting biomolecule or biomolecule complex structures, performing molecular replacement, and evaluating molecular replacement solutions until a superior search model has been identified.

The present invention will now be described in greater detail and in regard to the examples that follow.

1. Performing Molecular Replacement

Molecular replacement is performed by selecting a group of the structures to use as search models. As discussed elsewhere, selecting the group of structures may be performed manually or in an automated fashion. Selection may be based on a set of criteria (such as a degree of sequence identity) or may be random.

The group of structures used as search models preferably includes at least 3, 4, 5, 10, 15, 25, 50, 100, 200, 500, or more different structures.

The group also preferably includes at least 1, 2, 3, 4, 5, 10, 15, 25, 50, 100 or more different structures that are unlikely to have structural similarity with the biomolecule or biomolecule complex whose structure is being solved. An unlikelihood to have structural similarity may be based on the protein having less than 70%, preferably less than 50%, more preferably less than 40%, and most preferably less than 25% sequence identity with the protein whose structure is being solved.

Including at least one member of the group which is not likely to have structural similarity with the biomolecule or biomolecule complex whose structure is being solved can be achieved by selecting 2, 3, 4, 5, 10, 15, 25, 50, 100, or more structures for performing molecular replacement that are unlikely to have structural similarity with each other. Since the structures of the search models are known, an absence of structural similarity may be based on a comparison of their known structures. Computer programs such as CL, DALI, STRUCTAL, SSAP, or VAST may be used to perform these comparisons.

An absence of structural similarity may also be based on their lack of sequence identities. In this regard, at least two structures are preferably selected for performing molecular replacement that have less than 70%, preferably less than 50%, more preferably less than 40%, and most preferably less than 25% sequence identity with each other.

Selection of the members of the group may be performed before molecular replacement is performed on any member of the group or may be at least partially performed while molecular replacement is performed on other members of the group.

Selection may be part of an iterative process where additional members are added to the group until a superior search model is identified. In this regard, molecular replacement of members of the group may be performed and optionally additional members may be added to the group, until a superior search model is identified.

Selection of the members of the group may include a group of structures or fragments of structures that are known to have differences between themselves and other members of the group. Selection of the diverse group may be random or predetermined. A bias may be employed for selecting the group. For example, the bias may include a preponderance of alpha helical structures or beta sheet structures or structures containing a combination thereof, or structures not having identifiable substructures, or structures containing prosthetic groups, such as haemes or porphyrins or metal clusters.

The members of the group of structures upon which molecular replacement is performed may form all or a portion of a structure database, such as the Protein Data Bank. The members of the group of structures upon which molecular replacement is performed preferably forms at least 0.1%, 1% 5%, 10%, 20%, 30%, 40%, 50%, 75% or more of the Protein Data Bank. As the number of available solved protein structures gets larger and larger, the value of the present invention for accelerating the solution of protein structures increases.

Computational methods may also be used to generate search models. For example, predicted structures can be used as search models. As used herein, a predicted structure is one that is built as a model in a computer by manipulating coordinates but has no actual physical reality. An example would be a homology model built by changing the side chains of a known structure to the sequence of an unknown structure and then energy minimizing the model to resolve bumps between the new side chains. Another example would be taking a known structure and breaking into its component pieces, helices, sheets and loops, and then moving these loops with small translations and rotations to generate a family of similar structures to mimic what happens in the normal evolution of proteins between species.

In one embodiment, the group of different biomolecule structures on which molecular replacement searches are performed comprise at least 1, 2, 3, 4, 5, 10, 15, 25, 50, 100, 200, 500, or more different biomolecule structures that are predicted structures for a biomolecule.

Predicted models have not typically been used in molecular replacement searches because of the difficulty in assessing the validity of the resulting molecular replacement solution and the lack of an automated procedure for scoring large numbers of models relative to each other. However, by being able to assess search models based on a comparison of the resulting molecular replacement solutions in large numbers, one is able to readily evaluate different search models including search models based on predicted structures. Because the present invention allows the use of predicted structures as search models, it becomes feasible to employ predicted structures as some or all of the search models. For example, a first computer program can be used to generate a group of predicted structures while a second computer program performs molecular replacement searches using the predicted structures generated by the first program. Comparisons of the resulting solutions can then be used to identify which of the predicted structures are sufficiently structurally similar to the biomolecule whose structure is being solved.

Search models may also be generated for use in the present invention by analyzing structures where at least a portion of the native structure of the biomolecule has been removed. In one embodiment, the group of different biomolecule structures on which molecular replacement searches are performed may comprise at least 1, 2, 3, 4, 5, 10, 15, 25, 50, 100, 200, 500, or more different biomolecule structures where at least a portion of the native structure of the biomolecule has been removed.

In cases where a full structure contains regions not similar to the biomolecule whose structure is being solved, improved search models can be designed by omitting a portion of the search structure containing the dissimilar region. Hence, by taking a first group of structures, generating a second group of structures by subtracting one or more substructural elements from the structures in the first group, and performing molecular replacement searches on the structures in the second group (i.e., structures from the first group minus subtracted substructures), one is able to identify incomplete structures that are better search models than the corresponding complete structures.

Search models may also be generated for use in the present invention by analyzing different combinations of substructures. In one embodiment, the group of different biomolecule structures on which molecular replacement searches are performed may comprise at least 1, 2, 3, 4, 5, 10, 15, 25, 50, 100, 200, 500, or more different biomolecule structures which comprise a combination of two or more structure fragments.

In cases where a full structure contains regions not similar to the biomolecule whose structure is being solved, improved search models can be designed by analyzing different combinations of substructures. Hence, by forming a group of structures comprising different combinations of different substructures, and performing molecular replacement searches on the structures in the group, one is able to identify combinations of substructures that are better search models than available complete structures.

Once a group of search models are selected, molecular replacement is performed using each search model against the X-ray diffraction data for the biomolecule whose structure is being solved. Molecular replacement may be performed using a program such as EPMR, which is described herein in greater detail.

Given that molecular replacement is performed relative to multiple different structures, it may be desirable to take measures to perform the computations in a manner that saves time. For example, the multiple molecular replacements can be run sequentially on a single computer, or in parallel on multiple computers. If necessary, multiple CPUs may be used. Performing searches in parallel allows one to simultaneously search against a large number of structures all at once. Parallel searching may be performed using a parallel computer with a number of CPUs. Computations are performed until all search models in the group have been processed. If the number of members in the group exceeds the number of CPUs, each CPU performs multiple rounds until all the search models have been processed.

The molecular replacement may be performed using any available molecular replacement software, such as the program EPMR that is described herein in greater detail. In general, the molecular replacement software takes a given search model, rotates and translates the model randomly, and calculates the model's crystallographic amplitudes. These amplitudes are compared to the unknown crystallographic observed amplitudes using a correlation function. The best correlations are used to construct another generation of positions by mutation and crossover (i.e. a genetic algorithm). The process is preferably repeated for at least 50 generations. The best model is then rigid-body refined and the correlation and coordinates output.

Once molecular replacement on the group of search models has been completed, the results are collected and analyzed.

2. EPMR

A currently preferred program for performing molecular replacement is EPMR. It is noted however, that the present invention may be used in combination with any molecular replacement program since the present invention relates to the comparison on molecular replacement results as opposed to how molecular replacement itself is performed, such performance being well known in the art.

EPMR, its process and operation is described in detail in Rapid, Automated Molecular Replacement Using an Evolutionary Search Algorithm. Charles R. Kissinger, Daniel K. Gehlhaar and David B. Fogel *, Agouron Pharmaceuticals, Inc. 3565 General Atomics Court, San Diego, Calif. 92121 and * Natural Selection, Inc., 1591 Calle de Cinco, La Jolla, Calif. 92037.

The EPMR program operates as follows. An initial set of random solutions (random orientations and positions for the search model) is generated. A correlation coefficient is calculated for each orientation. A fraction of the highest scoring orientations are retained and used to regenerate a complete set of new trial orientations. This is done by applying random alterations to the orientation angles and translations for each 'surviving' solution. The correlation coefficients for the new population are calculated, the population is again regenerated from the top scoring solutions, and this procedure is repeated for a number of cycles. At the end of this evolutionary optimization, a traditional conjugate gradient minimization is performed. This is simply a rigid-body refinement of the atomic molecule orientation and position.

The use of an evolutionary algorithm allows for efficient searching of the six-dimensional space. It is several orders of magnitude faster than a brute-force, systematic search. The program calculates structure factors very quickly using the method of Huber and Schneider [J. Appl. Cryst. (1985) 18, 165–169]. A traditional structure factor calculation is done only once—for the search model set at the origin of a P1 box—and subsequent structure factor calculations are done by transforming reflection indices according to the rotations and translations applied to the model, interpolating into the grid of P1 structure factors and summing over the symmetry operators of the crystal. This is many times faster than an FFT calculation.

EPMR finds a single orientation for the search model in each run. In cases where one is looking for multiple molecules in the asymmetric unit, one must look for each solution sequentially. This can be done in two different ways. The program can be used to find the first solution and write it out. The first solution can then be entered as partial structure in subsequent runs. Alternatively, the program can be directed to find the first solution, keep it as partial structure, and keep going to look for as many solutions as desired. In this way, multi-body searches can be totally automatic.

The program requires three input files. The first is a file containing the cell constants and space group number in the order:

a b c alpha beta gamma space_group_number

These are free-format and can be divided between any number of lines. The program currently contains information only for the 65 enantiomorphic space groups. (For rhombohedral spacegroups, the hexagonal (obverse), not rhombohedral setting is used and your data needs to be indexed accordingly.) An example of appropriate contents for this file is:

40.76 18.49 22.33 90 90.61 90 4

The next input file is a standard PDB format file containing the search model (orthogonal Angstrom coordinates). Any lines in this input file that are not ATOM or HETATM records (e.g. REMARK lines, etc.) are ignored. Currently only scattering factors for C, N, O, S, P and FE are incorporated into the program. Atoms of other types are treated as if they are carbons, except for hydrogens, which are ignored.

The final input file contains the observed structure factors. The only requirement is that the file have H K L Fo as the first four items on each line, separated by spaces. XtalView "fin" format files work. These three files are all that are necessary to run the program. The command line: epmr example. cel example.pdb example.hkl will run the program in its default mode. In this mode, the program will search for a single molecule in the asymmetric unit. It will run the evolutionary search procedure up to ten times, or until a solution with a correlation coefficient of 0.5 is obtained. Data in the resolution range 15 to 4 Angstroms will be used in the search. The top solution found will be written to a file called 'epmr.1. best.pdb'.

The operation of the program can be controlled by the following set of command line options:

-m integer

This command refers to the number of identical molecules in the asymmetric unit for which to search. The default value is 1. The flag -m2 on the command line would cause the program to search for one solution, save it as partial structure and continue searching for a second solution.

-h real$_{13}$ number

This command sets the high resolution limit for diffraction data used in the search (in Angstroms). The default value is 4.0 Angstroms. It is not recommended for this value be set to greater than 5.0.

-l real$_{13}$ number

This command sets the low resolution limit for diffraction data (Angstroms). The default value is 15.0 Angstroms. The efficiency of the search appears to be aided slightly by the inclusion of low resolution data. If accurately measured low-resolution data is available, value of 25 or 30 may optionally be used.

-p integer

This command identifies the population size (number of trial solutions generated in each cycle). The default value is 300. Increasing this value beyond 300 seldom causes a dramatic improvement in search efficiency, but it never has a negative effect. IF the relative cost of computing is low, a value of "–p 600" can be chosen.

-g integer

This command identifies the number of 'generations' (cycles of optimization). The default value is 50. Increasing this value has much the same effect as increasing the population size, but the degree of improvement is even less predictable. It is not recommended that you change this value -n integer
 Number of runs.

The default value is 10. The program will stop before the completion of the number of runs specified here if a solution is obtained that has a correlation coefficient that exceeds a specified threshold (flag -t, below).

-t real_number

This command identifies a threshold value of the correlation coefficient that indicates an acceptable solution. Reaching the threshold value will stop the run. The default value is 0.5. If the -m flag has a value greater than 1, this default threshold is changed to 0.3. These values generally work well for a good search model. The program will stop when a solution correlation coefficient exceeds this threshold. If it is desired for the program to continue for a specified number of runs, this value should be set to 1.0. It is best to set this value relatively high to avoid having the program stop on an incompletely converged solution. In searches for multiple molecules in an asymmetric unit, the correlation coefficient for the top solution for the first molecule is scaled by 1.5 to obtain the threshold for the next molecule (unless that threshold would be lower than the originally specified threshold, in which case the original value is kept).

-T

This command instructs the program to operate in a translation only mode. This will cause the program to search only translation space, keeping the orientation of the search model unchanged. This could be useful, for instance, when one has a search model that has been pre-oriented by another program or through knowledge of non-crystallographic symmetry. Note that the orientation will be optimized during the final rigid-body optimization after the evolutionary search, so the orientation is likely to change slightly and could change significantly during this step.

-b real$_{13}$ number

This command identifies the minimum 'bump' distance— the smallest allowed distance between the center of mass of a solution and that of any symmetry mates. This is applied to all trial solutions that are generated during the course of the search. Any solution that violates this minimum distance is discarded. In the case of searches for multiple molecules in the asymmetric unit, this also sets the minimum distance between a solution and any previously found solutions. (This applies both to previous solutions found during the run and to partial structure entered with the -s option. See the description of the -s option below for instructions on entering multiple fragments of partial structure for use with this option.) This option thus provides a simple restriction on the packing of solutions, with little slowdown in the runtime of the program. This option clearly aids some searches, but decreases the efficiency of others. It appears to be less useful in single molecule searches than in searches for multiple molecules in the asymmetric unit, but should definitely be tried if ine is having trouble getting a solution that packs well. It is up to the operator to decide what an appropriate intermolecular distance should be. The default value is 0.0 (no packing restrictions).

-w integer

This command indicates the quantity of solutions that are to be written out to a PDB file. The default value is 1. A zero here means that no coordinates will be written out. A '1' means only the top solution from all of the runs will be written out. A '2' means the solution obtained from each run will be written out. The names of the output PDB files are controlled by the -o flag below.

-o name

This command identifies the file name prefix for the output coordinate files. The default is 'epmr'. If one specifies -w1 or -w2 above, the program will name the output files for each run as 'prefix'.'molecule_number'.'run_number'.pdb (e.g., epmr.1.1.pdb). The molecule number depends on how many molecules one is looking for in the asymmetric unit (option -m). The top solution from all of the runs will be 'prefix'.'molecule_number'.best.pdb. If multiple jobs are run in the same directory, this flag should be used to avoid writing over other solutions.

-s name

This command is a static partial structure flag. If one has a partial structure to input, include this flag and follow it with the name of the PDB file containing the correctly positioned partial structure. The partial structure can be separated into as many files as desired. Use this flag multiple times on the command line. It is only necessary to divide the partial structure up this way, however, if one is using the -b flag (see above) and are inputting multiple "pieces" of partial structure (e.g., multiple monomers). The minimum packing distance calculation will treat the partial structure within a single file as a single fragment.

-S

This command instructs the program to do the initial structure factor calculation by direct summation rather than FFT. This is a slower mode. If a very large search molecule is being used in combination with a workstation with little available memory, the FFT calculation may cause excessive swapping. Summation uses little memory. The program will print some information about the settings, do an initial FFT structure factor calculation, and then start the "evolution". It will report the best score for each generation. A conjugate-gradient minimization will then be performed on the best scoring solution from the final generation.

The final orientation for that run will be reported on a line that begins with 'Soln', followed by the run number, theta1, theta2, theta3 (Eulerian angles, defined as in X-PLOR), x translation, y translation, z translation in orthogonal Angstroms (If one intends to make use of these values outside of the program, they must be applied to the search model after it has been centered at the origin), and then the correlation coefficient and R factor. The UNIX command 'grep Soln log_file_name' can be used to print just the final solution generated by each run. For a single molecule in the asymmetric unit, expect a correlation coefficient of 0.5 or more for a correct solution with a pretty good search model. For the first of two in the asymmetric unit expect a cc above 0.30. Even poly-Ala and C-alpha models will have quite high correlation coefficients if they are accurate models.

3. Parallel Batch Processing of EPMR (P-EPMR):

A. Centralized Process Launch Method

This method consists of algorithms implemented in the C programming language which are designed to conserve the arguments normally used by the EPMR program and extend the capability of the program to take as input an entire directory of Protein Data Bank coordinate files and launch the processing of each file (by EPMR) on a separate Computer Cluster node. In effect, this method makes it possible to run these separate jobs (processes) in parallel, thus reducing the total time to process the data.

Note that the centralized process launch method has the disadvantage of a large latency between the first and the last batch job execution due to various system and network delays required to launch each job.

The standard EPMR command line was enhanced in the parallelized version to allow the input of an entire directory of input files. An example of the parallel epmr command ("pepmr") would be:

pepmr -r/sunhome/crystusr/epmr4millenia
-cmerk1.cel -kmerk1.hk1 -n1 -ipdb-culled-in parameters are as follows:
-r provides the main directory pathway
-c provides the CEL input file
-k provides the HKL input file
-n is the number of runs (same as EPMR)
-I is the PDB input directory Ultimately, these command parameters are processed by the P-EPMR program so as to generate the following individual batch job commands:

epmr-n1 /sunhome/crystusr/epmr4millenia/input/merk1.cel /sunhome/crystusr/epmr4millenia/pdb-temp /1EU1A.pdb /sunhome/crystusr/epmr4millenia/input/merk1.hkl >merk1.merk1.1EU1A.log &

This is the actual command which would end up running on a computer cluster node.

The algorithms perform the following tasks. The first step extracts various program control arguments that are normally part of the EPMR program and saves these to create each individual batch job command The next step determines which cluster nodes are available on the computer cluster and records their availability status. The next step generates a list of coordinate files from the PDB input directory. The next step is a loop which generates for each input file in the PDB coordinate directory list an actual batch job command string. This string is launched on a target node as a batch job. This step is repeated until a maximum number of processing jobs are running simultaneously on the cluster, at which point a status monitoring function determines if there are any available slots to run another job. If not, then the monitoring function directs the program to wait a short time interval, then to check again. This step is run repeatedly until all of the PDB coordinate input files have been processed as a batch job on the computer cluster.

The final step is a search step which searches the EPMR output files and sorts these as follows:

grep "CC="*/*.log | sort -nr+11

The average and the standard deviation of all of the CC (correlation coefficient) values are calculated from this list and the highest value compared to evaluate if a solution has been found as previously described.

B. Distributed Process Launch Method

The Distributed Process Launch method substantially reduces the latency between the first and last job launched in parallel on the computer cluster.

The idea behind this approach is to start up on each cluster node a separate set of subordinate server processes which perform commands directly on the node, instead of launching each process independently. A control process sends out commands to each of the subordinate nodes in the computer cluster, which in turn will start up and monitor the processing of EPMR on that node individually. The latency between the first and last job processed is substantially reduced because the control process does not need to wait for confirmation that each job has been launched, nor does it need to wait for the various system and network delays.

The Distributed Process Launch method has algorithms and tasks that are very similar to the Centralized Launch method described above, but a more complex infrastructure is developed in order to optimize performance. This infrastructure consists of algorithms to perform the tasks of determining which cluster nodes are available for use; and starting up (on each available computer cluster node) a separate subordinate server process.

The control process generates a series of commands based on inputs in a way similar to the algorithms described for the Centralized Process Launch method. However, each individual command is not directly executed from the control process, but rather, is sent as a message to a server process located on a cluster node where it is launched from the specific node's server process. Server processes on each node monitor the batch job execution and determine whether the job has completed. This status is relayed back to the control process which thus manages the cluster utilization. Batch jobs are thus launched until all input PDB files have been processed.

The final step is a search step which searches the EPMR output files and sorts these as follows:

grep "CC="*/*.log|sort -nr+11

4. Comparison of Molecular Replacement Solutions

Once molecular replacement solutions are generated using multiple different known structures as search models, the molecular replacement solutions are compared in order to identify, based on the molecular replacement solutions, which structure has superior structural identity with the biomolecule or biomolecule complex whose structure is being solved as compared to the other structures tested.

A structure that has "superior" structural identity with the biomolecule or biomolecule complex whose structure is being solved is preferably among the top 35%, 30%, 20% 10%, 5%, 2%, 1% or better structures tested.

A structure that has "superior" structural identity with the biomolecule or biomolecule complex whose structure is being solved is preferably at least two, three, four, five, ten or more standard deviations better than the other structures tested based on a comparison of their molecular replacement results.

Comparing molecular replacement solutions may be performed by any mathematical method that provides a correlation measurement between a given search model and the biomolecule or biomolecule complex whose structure is being solved based on a molecular replacement solution. Most typically, this correlation method will be based on correlation coefficient (C or C2) calculations for the molecular replacement solutions.

$$C = \frac{\sum (Fo - \overline{Fo})(Fc - \overline{Fc})}{\sqrt{\sum (Fo - \overline{Fo})^2 \sum (Fc - \overline{Fc})^2}}$$

$$C2 = \frac{\sum FoFc}{\sqrt{\sum Fo^2 \sum Fc^2}}$$

According to Parseval's theorem, the root mean square ("rms") error in an electron density map is proportional to the rms error in the corresponding structure factor. In order to minimize the rms error in electron density, one therefore must find the structure factor that minimizes the rms error in the complex plane. Blow and Crick showed that, if something is known about the probabilities of different possible phase choices, the rms error can be minimized in the structure factor by taking its probability-weighted average over all possible phase choices.

The process of taking a probability-weighted average is illustrated in FIG. 1. The circle represents possible values for the complex structure factor F, with its different possible phase choices. The probability of each possible phase is indicated by the thickness of the line around the circle. Averaging a complex number around a circle gives a complex number inside the circle, i.e. one with a smaller magnitude than the radius of the circle. This average complex number also has a phase, which Blow and Crick termed the "best phase". The reduction in the amplitude is expressed through a number called the figure of merit, m.

For perfect phase information, the figure of merit and the correlation coefficient (C) is 1. As the phase information becomes more ambiguous, the figure of merit and the correlation coefficient drop, until they become zero or less then 0 (for a correlation coefficient) when all phases are equally probable and there is no correlation between the predicted and observed amplitudes. The problem with figures of merit and correlation coefficient prior to the present invention is that a given correlation coefficient lacks a reference point to indicate how good a given correlation coefficient is. By contrast, by calculating correlation coefficient using multiple different structures as search models, one is able to effectively calibrate a given correlation coefficient relative to other search models. By including poor search models in the calibration, a baseline for structurally dissimilar search models is created. As can be seen on the left hand side of the graphs shown in FIGS. 2 and 3, when structurally similar search models are identified, they can be very readily recognized.

Figure 2:
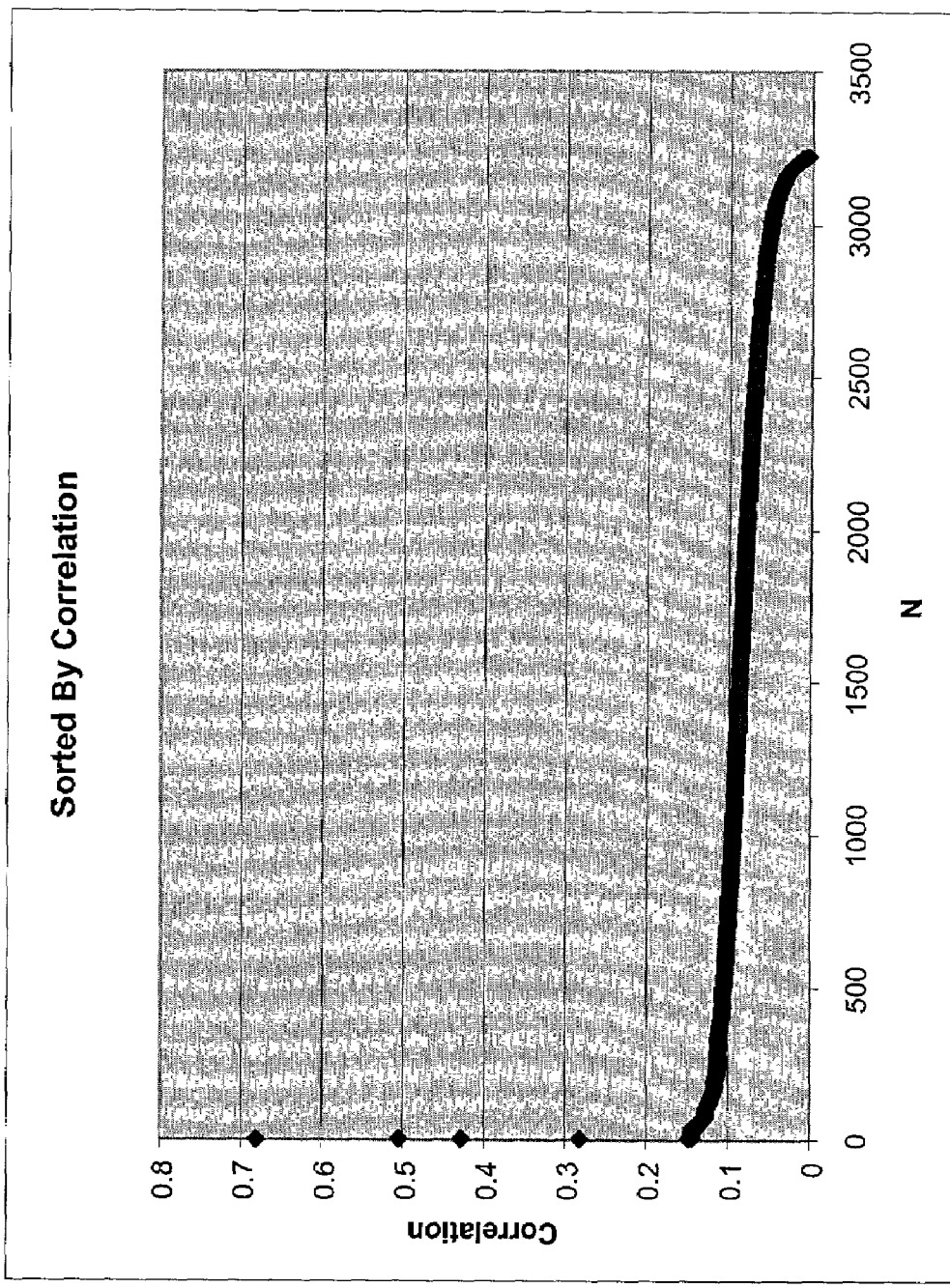
FIG. 2 shows the results of a PEPMR run with a target dataset of a xylose isomerase dataset and all of the proteins in the Protein Data Bank more than 80% different as of February 2000 (3245 structures).

FIG. 2 shows the results of a PEPMR run with a target dataset of a xylose isomerase dataset and all of the proteins in the Protein Data Bank more than 80% different as of February 2000 (3245 structures). The run took about 90 minutes of a 470-node 800 Mhz Pentium III LINUX cluster. The correlation coefficient of each epmr "solution" (blue points) was sorted from the highest (left) to lowest (right). The 4 points on the left represent 4 true solutions. The top one is the identical xylose isomerase as previously solved in the Protein Data Bank, and the next three highest are related xylose isomerases, with 68%, 65% and 53% sequence identity respectively.

Figure 3:
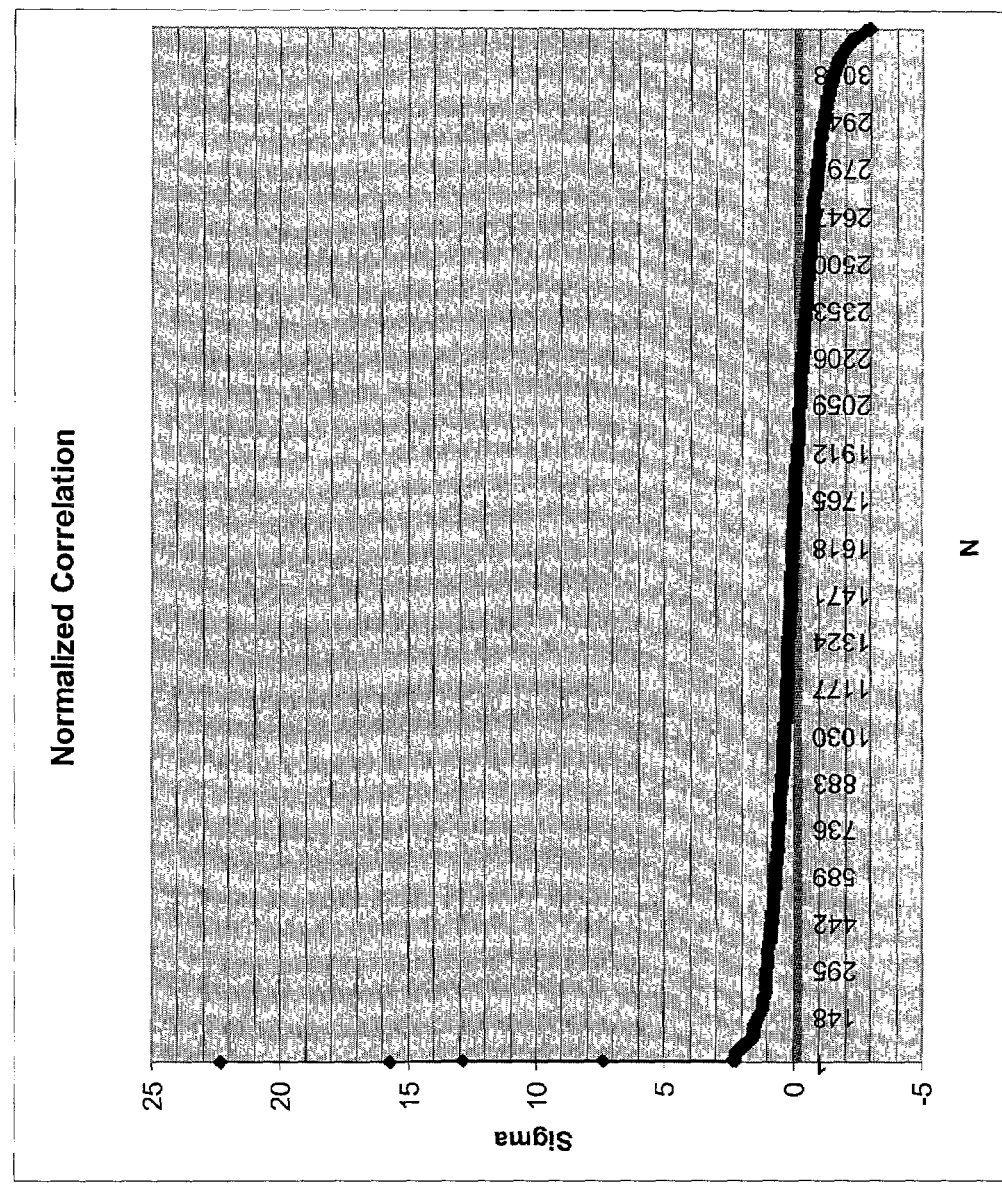
FIG. 3 shows the same results as shown in FIG. 2 except that the result are normalized so that one standard deviation equals one and the average is 0.

FIG. 3 shows the same results as shown in FIG. 2 except that the result are normalized so that one standard deviation equals one and the average is 0. Note that the background solutions are all well within +/−3 sigma. The four solutions are located at 22, 16, 13 and 7 times sigma.

Without comparing figures of merit, one can have one or more figures of merit that appear to be relevant. As illustrated in FIG. 3, the comparison and thus calibration of correlation coefficients overcomes the significant problem of not being able to recognize that none of the search models provide a good fit with the biomolecule whose structure is being solved. Few solutions are found to be more than 2 times the standard deviation. As seen in FIG. 3, only four solutions out of over 3000 are above 2.5 times the standard deviation (at 7×, 13×, 16×, and 22×). These few solutions are highly likely to be significant and almost certainly a solution.

There exist other methods for comparing structures to data. These methods can be divided into three major sub groups; those that are based upon correlations of the phases, those that are based upon correlations of the intensities or functions of intensities (e.g. Fs), and those that are based upon correlations in 'real space'. The standard figure of merit is an analysis of the relative match of the observed amplitudes and the predicted amplitudes from the location and orientation of the search model. This figure of merit is typically computed as a simple least squares analysis of the comparison between $F_c(hkl)$ and $F_o(hkl)$, where the $F_c$ represents the calculated structure factor and $F_o$ represent the observed structure factor at a given reflection, hkl. This can be expressed as $$r^2 = \frac{\sum_{hkl}(F_{c_{hkl}} - F_{o_{hkl}})^2}{\sum_{hkl}(F_{o_{hkl}})^2},$$

which is a simple variation on a least squares estimate, through normalizing the value through the sum of the square values.

A similar linear residual is $$r = \sum_{hkl}(F_{c_{hkl}} - F_{o_{hkl}}).$$

One can compute other correlations based upon more complex functions of the data, such as simple powers of the differences e.g. Different methods have different relative strengths, but all the methods compute an index or groups of indices that describe the relative match of the search model with the target data set. There are also secondary estimates of the quality of the solution, and therefore the correlation of the search model with the target data and these include further refinement of the search model against the target data and the standard analytic correlations, such as the refinement R-factor, the R-free and analyses of B-factors. A common expression for the crystallographic R-factor is $$R_{crystallographic} = \frac{\sum_{hkl}|(F_{c_{hkl}} - F_{o_{hkl}})|}{\sum_{hkl}|(F_{o_{hkl}})|}$$

Any method which ranks the goodness of fit between the search model and the observed data can be used to evaluate the success of the molecular replacement.

It is important to note that since all of the methods map multidimensional data onto a lower dimensional space or a single number that there multiple ranking methods which will produce equivalent rankings.

4. Determining Molecular Replacement Solutions For Substructures

To alleviate this, the model can be broken into its component parts, helices and sheets, and each part assigned its own control values (translation on the three orthogonal axes x, y, z, and three rotations about each of these axes) and these can be systematically and randomly varied to find the optimal solution.

In between cycles the top hits can be recombined between the best models to produce a hybrid model. This is equivalent to recombining the structures in a genetic sense although only the control variables need be swapped in actual practice. The new set of models is then used in a parallel replacement and the process repeated to convergence.

Structural elements of the model can also be randomly removed—i.e. the occupancies set to 0 or alternatively the B-values set very high to "smear" their density. These can be included as variables in the genetic algorithm search and recombined between runs as above.

5. Iterative Search For Suitable Search Model

An iterative search can be done by using one program to genrate a family of models. These models are then scored by the PEPMR process described above and sorted. The top few models are then used as the basis of constructing a new generation of models by duplicating, mutating and recombining between models. This next generation is scored and the cycle repeated until a good score (i.e. 2, 3, 4, or more times the background sigma) is found or the process converges.

6. Solving Crystal Structure Using Molecular Replacement Solution From Selected Search Model After a molecular replacement solution is found the model is improved by iterative steps of fitting the model to the map (changing the model to best fit the electron density as on a graphics screen using a "fitting" program such as Xfit or O) and then refined against the data using a refinement program such as TNT, SHELX, REFMAC or CNS/XPLOR. This procedure can be done in an automated way by the program wARP/ARP if the data is above 2 Å or can be done "manually" below this resolution.

7. Validation of Molecular Replacement Solutions

The invention can be used in conjunction with protein classification systems, such as SCOP (SCOP: Structural Classification of Proteins, currently at http://scop.berkelev.edu/) to produce disparate groups of unrelated structures for the purposes of assessing the validity of molecular replacement solutions. Protein classification systems such as SCOP use the protein structure to organize proteins into families and super-families of fold. These programs produce a hierarchy of proteins based upon the degree that the proteins are structurally related. Thus, one can select from these family trees of proteins those proteins belonging to disparate groups. The proteins selected from disparate groups can then be used as minimally spanning basis set in the structure solution space. One can use these disparate families to provide information both to inform which family of proteins might form the basis of a correct solution, and also to inform statistically relevant score for an incorrect solution. Moreover, once a good solution is found, additional searches could be run with proteins know to be structurally related, whether or not there was any sequence relation between the members of a family within the classification of the protein structures.

The minimally spanning basis can be determined by statistical methods, wherein one solution is known to match the unknown, and then a series of structurally unrelated proteins are sequentially included, allowing one to define the minimal number of protein structures needed to search against to define a statistically significant result. In the unknown case, the basis forms the minimal number of protein structures against which one must search in order to define a solution as likely to be correct.

8. Molecular Replacement On Crystal Data Other Than X-ray Crystal Data

Although the various methods and software for making comparisons between molecular replacement solutions performed according to the present invention is described above with regard to using X-ray diffraction data, it is noted that other forms of data can also be employed other than X-ray diffraction data. For example, neutron diffraction data, nuclear magnetic resonance data, and mass spectroscopy data may also be employed.

In one embodiment, a method is provided for determining a structure of a target biomolecule, the method comprising: employing computer executable logic to perform multiple molecular replacement searches on data of the target biomolecule other than X-ray diffraction data where a group of different biomolecule structures are used as search models for the multiple molecular replacement searches; employing computer executable logic to identify a biomolecule structure from the group whose use as a search model produces a molecular replacement solution that is superior to the molecular replacement solutions produced by the other biomolecule structures in the group; and employing computer executable logic to determine a structure for the target biomolecule employing the identified biomolecule structure.

In another embodiment, computer readable medium is provided that is useful in association with a computer which includes a processor and a memory, the computer readable medium comprising: logic for performing multiple molecular replacement searches on data of the target biomolecule other than X-ray diffraction data where a group of different biomolecule structures are used as search models for the multiple molecular replacement searches; and logic for identifying a biomolecule structure from the group whose use as a search model produces a molecular replacement solution that is superior to the molecular replacement solutions produced by the other biomolecule structures in the group.

In another embodiment, a method is provided for determining a structure of a target biomolecule, the method comprising: employing computer executable logic to perform multiple molecular replacement searches on data of the target biomolecule other than X-ray diffraction data where a group of different biomolecule structures are used as search models for the multiple molecular replacement searches; employing computer executable logic to identify a biomolecule structure from the group whose use as a search model produces a molecular replacement solution that is superior to the molecular replacement solutions produced by the other biomolecule structures in the group; and employing computer executable logic to determine a structure for the target biomolecule employing the identified biomolecule structure.

In yet another embodiment, computer readable medium is provided that is useful in association with a computer which includes a processor and a memory, the computer readable medium comprising: logic for performing multiple molecular replacement searches on data of the target biomolecule other than X-ray diffraction data where a group of different biomolecule structures are used as search models for the multiple molecular replacement searches; logic for identifying a biomolecule structure from the group whose use as a search model produces a molecular replacement solution that is superior to the molecular replacement solutions produced by the other biomolecule structures in the group; and logic for determining a structure for the target biomolecule employing the identified biomolecule structure.

In yet another embodiment, a method is provided for identifying a search model to use in molecular replacement for determining a structure of a target biomolecule, the method comprising: (a) employing computer executable logic to perform multiple molecular replacement searches on data of the target biomolecule other than X-ray diffraction data using multiple different biomolecule structures as search models; (b) employing computer executable logic to compare the resulting molecular replacement solutions in order to identify a biomolecule structure whose use as a search model produces a molecular replacement solution that is superior to the molecular replacement solutions of other biomolecule structures upon which the molecular replacement searches were performed; and (c) if none of the molecular replacement solutions are comparatively better, evaluating additional biomolecule structures by repeating steps (a) and (b) with the additional biomolecule structures until a biomolecule structure is identified which produces a molecular replacement solution that is superior to the molecular replacement solutions of other biomolecule structures upon which the molecular replacement searches were performed.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method for identifying a search model to use in molecular replacement for determining a structure of a target biomolecule from crystal data, the method comprising:
   employing first computer executable logic to perform multiple molecular replacement searches on crystal data of the target biomolecule where a group of structures of different biomolecules are used as search models for the multiple molecular replacement searches; and
   employing second computer executable logic to compare the molecular replacement solutions produced by the first computer executable logic, the comparison producing data that predicts which biomolecule structures in the group have superior structural identity with the target biomolecule as compared to the other biomolecule structures in the group.

2. A method according to claim 1 wherein comparing molecular replacement solutions comprises comparing figures of merit calculated for the molecular replacement solutions.

3. A method according to claim 2 wherein comparing molecular replacement solutions comprises performing a statistical analysis on figures of merit calculated for the molecular replacement solutions.

4. A method according to claim 2 wherein comparing molecular replacement solutions comprises determining which of the biomolecule structures in the group produced a molecular replacement solution whose figure of merit is at least two standard deviations better than the average figure of merit for molecular replacement solutions for the biomolecule structures in the group.

5. A method according to claim 2 wherein comparing molecular replacement solutions comprises determining which of the biomolecule structures in the group produced a molecular replacement solution whose figure of merit is at least three standard deviations better than the average figure of merit for molecular replacement solutions for the biomolecule structures in the group.

6. A method according to claim 2 wherein comparing molecular replacement solutions comprises determining which of the biomolecule structures in the group produced a molecular replacement solution whose figure of merit is at least five standard deviations better than the average figure of merit for molecular replacement solutions for the biomolecule structures in the group.

7. A method according to claim 2 wherein comparing molecular replacement solutions comprises determining which of the biomolecule structures in the group produced a molecular replacement solution whose figure of merit is at least ten standard deviations better than the average figure of merit for molecular replacement solutions for the biomolecule structures in the group.

8. A method according to claim 1 wherein comparing molecular replacement solutions comprises comparing root mean square errors for each molecular replacement solution of a probability-weighted average over all possible phase choices.

9. A method according to claim 1 wherein comparing molecular replacement solutions comprises establishing a background correlation level between the biomolecule structures in the group and the target biomolecule based on the molecular replacement solutions and determining which of the biomolecule structures in the group produced a molecular replacement solution that exceeds the background correlation level by at least two standard deviations.

10. A method according to claim 1 wherein comparing molecular replacement solutions comprises establishing a background correlation level between the biomolecule structures in the group and the target biomolecule based on the molecular replacement solutions and determining which of the biomolecule structures in the group produced a molecular replacement solution that exceeds the background correlation level by at least three standard deviations.

11. A method according to claim 1 wherein comparing molecular replacement solutions comprises establishing a background correlation level between the biomolecule structures in the group and the target biomolecule based on the molecular replacement solutions and determining which of the biomolecule structures in the group produced a molecular replacement solution that exceeds the background correlation level by at least five standard deviations.

12. A method according to claim 1 wherein comparing molecular replacement solutions comprises establishing a background correlation level between the biomolecule structures in the group and the target biomolecule based on the molecular replacement solutions and determining which of the biomolecule structures in the group produced a molecular replacement solution that exceeds the background correlation level by at least ten standard deviations.

13. A method according to claim 1 wherein the group of different biomolecule structures on which molecular replacement searches are performed comprises at least 3 different biomolecule structures.

14. A method according to claim 1 wherein the group of different biomolecule structures on which molecular replacement searches are performed comprises at least 0.1% of the protein structures stored in the Protein Data Bank.

15. A method according to claim 1 wherein the group of different biomolecule structures on which molecular replacement searches are performed comprises at least one biomolecule structure that has less than 70% sequence identity with the target biomolecule.

16. A method according to claim 1 wherein the group of different biomolecule structures on which molecular replacement searches are performed comprises structures of at least two different biomolecules that are sufficiently structurally dissimilar to each other that the structure of the at least two different biomolecules would not both be effective search models for a same target molecule.

17. A method according to claim 1 wherein the group of different biomolecule structures on which molecular replacement searches are performed comprises at least two different biomolecule structures that have less than 70% sequence identity with each other.

18. A method according to claim 1 wherein the group of different biomolecule structures on which molecular replacement searches are performed comprises at least one predicted structure for a biomolecule.

19. A method according to claim 1 wherein the group of different biomolecule structures on which molecular replacement searches are performed comprises at least one structure where at least a portion of the native structure has been removed.

20. A method according to claim 1 wherein the group of different biomolecule structures on which molecular replacement searches are performed comprises at least one structure which comprises a combination of two or more structure fragments.

21. A method according to claim 1 wherein the data produced from the comparison identifies which biomolecule structures produced molecular replacement solutions that have a figure of merit at least among the top 35% of molecular replacement solutions produced by the group.

22. A method according to claim 1 wherein the data produced from the comparison identifies which biomolecule structures produced molecular replacement solutions have a figure of merit that is at least two standard deviations better than the molecular replacement solutions produced by the group.

23. A method according to claim 1 wherein the data produced from the comparison identifies which biomolecule structures produced molecular replacement solutions have a figure of merit that is at least three standard deviations better than the molecular replacement solutions produced by the group.

24. A method according to claim 1 wherein the data produced from the comparison identifies which biomolecule structures produced molecular replacement solutions have a figure of merit that is at least five standard deviations better than the molecular replacement solutions produced by the group.

25. A method according to claim 1 wherein the data produced from the comparison identifies which biomolecule structures produced molecular replacement solutions have a figure of merit that is at least ten standard deviations better than the molecular replacement solutions produced by the group.

26. A method according to claim 1, further comprising employing computer executable logic to select the group of different biomolecule structures used to perform the multiple molecular replacement searches.

27. A method according to claim 26 wherein selection of the group of biomolecule structures is based, at least in part, on sequence identity between the biomolecule structure and the target biomolecule.

28. A method according to claim 26 wherein selection of the group of biomolecule structures is at least partially random.

29. A method according to claim 26 wherein selection of the group of biomolecule structures is completely random.

30. A method according to claim 26 wherein selection of the group of biomolecule structures is iterative.

31. A method according to claim 26 wherein selection of members of the group of biomolecule structures is performed until a biomolecule structure is selected whose molecular replacement solution is at least two standard deviations better than the average molecular replacement solution for the biomolecule structures in the group.

32. A method according to claim 26 wherein selection of members of the group of biomolecule structures is performed until a biomolecule structure is selected whose molecular replacement solution is at least three standard deviations better than the average molecular replacement solution for the biomolecule structures in the group.

33. A method according to claim 26 wherein selection of members of the group of biomolecule structures is performed until a biomolecule structure is selected whose molecular replacement solution is at least five standard deviations better than the average molecular replacement solution for the biomolecule structures in the group.

34. A method according to claim 26 wherein selection of members of the group of biomolecule structures is performed until a biomolecule structure is selected whose molecular replacement solution is at least ten standard deviations better than the average molecular replacement solution for the biomolecule structures in the group.

35. A method according to claim 26 wherein selection of the group of biomolecule structures comprises selecting at least 0.1% of the structures stored in the Protein Data Bank.

36. A method according to claim 1 wherein selection of the group of biomolecule structures comprises selecting at least one biomolecule structure that has less than 70% sequence identity with the target biomolecule.

37. A method according to claim 1 wherein selection of the group of biomolecule structures comprises selecting at least two biomolecule structures that are structurally dissimilar.

38. A method according to claim 1 wherein selection of the group of biomolecule structures comprises selecting at least two biomolecule structures that have less than 70% sequence identity with each other.

39. A method according to claim 1 wherein molecular replacement is performed using a program selected from the group consisting of AMoRe, BRUTE, COMO, wARP, moI-REP, EPMR, XPLOR, CNS, TNT, GLRF, TRANSF, TF, ENVELOPE, FFSYNTH, FFTINV, FFTEXP, and RECIP.

40. A method according to claim 1 wherein molecular replacement is performed using EPMR.

41. A method according to claim 1 wherein molecular replacement is performed using a molecular replacement program comprising an evolutionary algorithm for searching six-dimensional space.

42. A method according to claim 1 wherein the biomolecule is a protein.

43. A method according to claim 1 wherein the biomolecule is a DNA.

44. A method according to claim 1 wherein the biomolecule is a RNA.

45. A method according to claim 1 wherein the biomolecule is a complex comprising a protein.

46. A method according to claim 1 wherein the biomolecule is a complex comprising DNA.

47. A method according to claim 1 wherein the biomolecule is a complex comprising RNA.

48. A method according to claim 1 wherein the crystal data is X-ray diffraction data.

49. A method according to claim 1 wherein the crystal data is neutron diffraction crystal data.

50. A method according to claim 1 wherein the crystal data is nuclear magnetic resonance crystal data.

51. A method according to claim 1 wherein the crystal data is mass spectroscopy crystal data.

52. A computer readable medium useful in association with a computer which includes a processor and a memory, the computer readable medium comprising:

first logic for performing multiple molecular replacement searches on crystal data of a target biomolecule where a group of structures of different biomolecules are used as search models for the multiple molecular replacement searches; and second logic which takes results of the multiple molecular replacement searches performed by the first logic and compares solutions from the multiple molecular replacement searches, the comparison producing data that predicts which biomolecule structures from the group have superior structural identity with the target biomolecule as compared to the other biomolecule structures in the group.

53. A method for identifying a search model to use in molecular replacement for determining a structure of a target biomolecule from crystal data, the method comprising:

employing first computer executable logic to perform multiple molecular replacement searches on crystal data of the target biomolecule where a group of structures of different biomolecules are used as search models for the multiple molecular replacement searches; and employing second computer executable logic to predict based on the molecular replacement solutions produced by the first computer executable logic a biomolecule structure from the group whose use as a search model will produce a molecular replacement solution that is superior to the molecular replacement solutions produced by the other biomolecule structures in the group.

54. A computer readable medium useful in association with a computer which includes a processor and a memory, the computer readable medium comprising:

first logic for performing multiple molecular replacement searches on X-ray diffraction data of a target biomolecule where a group of structures of different biomolecules are used as search models for the multiple molecular replacement searches; and second logic which takes results of the multiple molecular replacement searches performed by the first logic and predicts which biomolecule structure from the group whose use as a search model will produce a molecular replacement solution that is superior to the molecular replacement solutions produced by the other biomolecule structures in the group.

55. A method for determining a structure of a target biomolecule from crystal data, the method comprising:

employing first computer executable logic to perform multiple molecular replacement searches on crystal data of the target biomolecule where a group of structures of different biomolecules are used as search models for the multiple molecular replacement searches;

employing second computer executable logic to predict based on the molecular replacement solutions produced by the first computer executable logic a biomolecule structure from the group whose use as a search model will produce a molecular replacement solution that is superior to the molecular replacement solutions produced by the other biomolecule structures in the group; and employing computer executable logic to determine a structure for the target biomolecule employing the identified biomolecule structure.

56. A computer readable medium useful in association with a computer which includes a processor and a memory, the computer readable medium comprising:

first logic for performing multiple molecular replacement searches on crystal data of a target biomolecule where a group of structures of different biomolecules are used as search models for the multiple molecular replacement searches;

second logic which takes results of the multiple molecular replacement searches performed by the first logic and predicts which biomolecule structure from the group whose use as a search model will produce a molecular replacement solution that is superior to the molecular replacement solutions produced by the other biomolecule structures in the group; and third logic for determining a structure for the target biomolecule employing the identified biomolecule structure.

57. A method for identifying a search model to use in molecular replacement for determining a structure of a target biomolecule from crystal data, the method comprising:

(a) employing first computer executable logic to perform multiple molecular replacement searches on crystal data of the target biomolecule using structures of different biomolecules as search models;

(b) employing second computer executable logic to compare the molecular replacement solutions produced by the first computer executable logic in order to predict a biomolecule structure from among the structures with whom the multiple molecular replacement searches were performed whose use as a search model will produce a molecular replacement solution that is superior to the molecular replacement solutions of other biomolecule structures upon which the molecular replacement searches were performed; and (c) if none of the molecular replacement solutions are comparatively better, evaluating additional biomolecule structures by repeating steps (a) and (b) with the additional biomolecule structures until a biomolecule structure is identified which is predicted to produce a molecular replacement solution that is superior to the molecular replacement solutions of other biomolecule structures upon which the molecular replacement searches were performed.

* * * * *